(12) United States Patent
Groebke Zbinden et al.

(10) Patent No.: US 9,708,302 B2
(45) Date of Patent: Jul. 18, 2017

(54) FLOURO-NAPHTHYL DERIVATIVES

(71) Applicant: Hoffmann-La Roche Inc., Little Falls, NJ (US)

(72) Inventors: Katrin Groebke Zbinden, Liestal (CH); Emmanuel Pinard, Linsdorf (FR); Thomas Ryckmans, Rosenau (CH)

(73) Assignee: HOFFMANN-LA-ROCHE INC., Little Falls, NJ (US)

( * ) Notice: Subject to any disclaimer, the term of this patent is extended or adjusted under 35 U.S.C. 154(b) by 0 days.

(21) Appl. No.: 15/216,435

(22) Filed: Jul. 21, 2016

(65) Prior Publication Data

US 2016/0326144 A1   Nov. 10, 2016

Related U.S. Application Data

(63) Continuation of application No. PCT/EP2015/050830, filed on Jan. 19, 2015.

(30) Foreign Application Priority Data

Jan. 22, 2014   (EP) .................................... 14152124

(51) Int. Cl.
| | |
|---|---|
| *C07D 405/02* | (2006.01) |
| *C07D 405/14* | (2006.01) |
| *C07D 213/61* | (2006.01) |
| *C07D 213/56* | (2006.01) |
| *C07D 309/14* | (2006.01) |
| *C07D 401/04* | (2006.01) |
| *C07D 405/12* | (2006.01) |

(52) U.S. Cl.
CPC ......... *C07D 405/14* (2013.01); *C07D 213/56* (2013.01); *C07D 213/61* (2013.01); *C07D 309/14* (2013.01); *C07D 401/04* (2013.01); *C07D 405/12* (2013.01)

(58) Field of Classification Search
None
See application file for complete search history.

(56) References Cited

U.S. PATENT DOCUMENTS

2012/0041036 A1* 2/2012 Kinoyama ............ C07C 279/22
514/357

FOREIGN PATENT DOCUMENTS

| | | |
|---|---|---|
| WO | 2005/033072 A2 | 4/2005 |
| WO | 2011/149801 A1 | 12/2011 |

OTHER PUBLICATIONS

Bernstein P.R. et al., "Discovery of Novel, Orally Active Dual NK1/NK2 Antagonists" Bioorganic & Medicinal Chemistry Letters 11(20):2769-2773 (Oct. 22, 2001).
ISR for PCT/EP2015/050830.
Yuguang Wang et al., "Sulfide Analogues as Potent and Selective M2 Muscarinic Receptor Antagonists" Bioorganic & Medicinal Chemistry Letters 12:1087-1091 (Apr. 8, 2002).

* cited by examiner

*Primary Examiner* — Nyeemah A Grazier
(74) *Attorney, Agent, or Firm* — Genentech, Inc.; Mark D. Kafka

(57) ABSTRACT

The present invention relates to compounds of formula

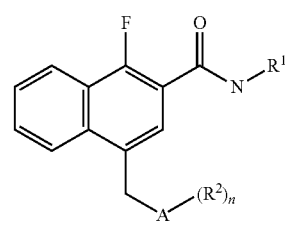

I wherein
$R^1$ is $C_{4-6}$-cycloalkyl or $C_{4-6}$-heterocycloalkyl, which are optionally substituted by one or two substituents, selected from hydroxy or lower alkyl;
A is phenyl, pyridinyl or piperidinyl;
$R^2$ is hydrogen, halogen, lower alkyl, cyano, $C_{4-6}$-cycloalkyl, lower alkoxy, lower alkoxy substituted by halogen, or is a five- or six-membered heteroaryl, optionally substituted by lower alkyl;
n is 1 or 2;
or to a pharmaceutically acceptable acid addition salt, to a racemic mixture or to its corresponding enantiomer and/or optical isomers thereof.
The compounds may be used for the treatment or prophylaxis of Alzheimer's disease, cognitive impairment, schizophrenia, pain or sleep disorders.

12 Claims, No Drawings

FLOURO-NAPHTHYL DERIVATIVES

CROSS-REFERENCE TO RELATED APPLICATIONS

This application is a continuation of International Patent Application No. PCT/EP2015/050830 filed Jan. 19, 2015 which claims priority to European Patent Application No. 14152124.5, filed on Jan. 22, 2014, the entire contents of which are incorporated by reference in its entirety.

The present invention relates to compounds of formula

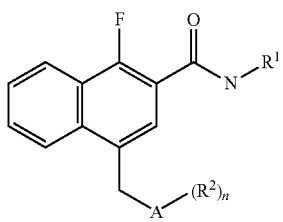

I wherein
$R^1$ is $C_{4-6}$-cycloalkyl or $C_{4-6}$-heterocycloalkyl, which are optionally substituted by one or two substituents, selected from hydroxy or lower alkyl;
A is phenyl, pyridinyl or piperidinyl;
$R^2$ is hydrogen, halogen, lower alkyl, cyano, $C_{4-6}$-cycloalkyl, lower alkoxy, lower alkoxy substituted by halogen, or is a five- or six-membered heteroaryl group, optionally substituted by lower alkyl;
n is 1 or 2;
or to a pharmaceutically acceptable acid addition salt, to a racemic mixture or to its corresponding enantiomer and/or optical isomers thereof.

WO 2011149801 describes similar compounds for treating neurological and psychiatric disorders associated with muscarinic acetylcholine receptor dysfunction. The activity ($EC_{50}$ in nM) is about 2 or more times lower, and therefore these compounds are less suitable for the development of corresponding drugs. The F-substitution on the naphthyl ring instead of $OR^1$ in WO 2011149801 leads to more active compounds, which could not predicted.

The compounds of the present invention are muscarinic M1 receptor positive allosteric modulators (PAM) and hence are useful in the treatment of diseases, mediated by the muscarinic M1 receptor, such as Alzheimer's disease, cognitive impairment, schizophrenia, pain or sleep disorders.

Acetylcholine (ACh) is a neurotransmitter which activates both nicotinic (ligand-gated ion channel) and muscarinic (metabotropic) receptors in the CNS and in the periphery.

The muscarinic receptors (mAChRs) are members of the class A G-protein-coupled receptors. To date, five distinct subtypes of mAChRs (M1-M5) have been cloned and sequenced. The muscarinic M1 receptors are predominantly distributed in the brain, with the highest expression in the cortex, thalamus, striatum and hippocampus. In clinical studies, Xanomeline, a M1/M4-preferring agonist, demonstrated robust efficacy on positive, negative and cognitive symptoms in schizophrenic patients and improved cognitive scores and reduced psychotic-like behaviors in patients with Alzheimer's disease (AD). The M1 receptor has been implicated in memory and learning processes, regulation of dopamine and NMDA receptor activity and has thus been proposed as a potential target for the treatment of AD and schizophrenia.

AD is the most common cause of dementia in later life. Pathologically AD is characterized by the deposition in the brain of amyloid in extracellular plaques and intracellular neurofibrillary tangles. The amyloid plaques are mainly composed of amyloid peptides (Abeta peptides) which originate from the β-Amyloid Precursor Protein (APP) by a series of proteolytic cleavage steps. Several forms of APP have been identified of which the most abundant are proteins of 695, 751 and 770 amino acids length. They all arise from a single gene through differential splicing. The Abeta peptides are derived from the same domain of the APP but differ at their N- and C-termini, the main species are of 40 and 42 amino-acid length by processing of the beta-amyloid precursor protein (APP) by the beta-amyloid protein cleaving enzyme. The processing leads to accumulation of Abeta in the brain.

M1 receptors are abundantly expressed postsynaptically in cortex, hippocampus and striatum which are important brain regions involved for cognition. Based on the cholinergic hypothesis i.e. degeneration of presynaptic cholinergic nerve terminals in hippocampus and cortical regions, M1 activation should rescue the cognitive deficits which occur in AD, thus providing symptomatic treatment of this neurodegenerative disorder. Postmortem studies in AD cortical tissues have shown that M1 receptor expression are not reduced, thus providing evidence for target availability in a critical brain region. Moreover, preclinical studies have shown that M1 activation has potential as a disease-modifying therapy for AD by shifting the APP processing towards the non-amyloidogenic α-secretase pathway and by decreasing tau hyperphosphorylation. Therefore, M1 PAMs provide an approach to target both symptomatic and disease-modifying treatment of AD.

Schizophrenia is a severe, disabling, lifelong disorder that affects 1% of the population and is characterized by positive symptoms (such as hallucinations, delusions and paranoia), negative symptoms (such as social withdrawal and apathy) and cognitive impairment (for example, deficits in working memory, executive function and attention). Schizophrenia is a neurodevelopmental disorder with genetic risk factors and neuropathological changes. Aberrant activity occurs within the prefrontal-hippocampal-thalamic network in brains of schizophrenia patients. Positive symptoms of schizophrenia are suggested to be caused by dopaminergic system dysfunction, particularly increased dopamine activity within subcortical brain regions such as the striatum. Negative symptoms are thought to occur due to impaired signaling within the neurocircuitry of the ventral segmental area and ventral striatum. Decreased NMDA receptor function in pyramidal neurons coupled with sub-optimal dopamine release in critical regions such as dorsolateral prefrontal cortex may account for some of the cognitive deficits.

M1 receptors are located in regions which are affected in schizophrenia, such as the hippocampus, cortex and striatum, in particular in the medium spiny neurons. Several reports have shown a reduction in muscarinic receptors in the prefrontal cortex and hippocampus, regions where M1 is densely expressed, in a subset of schizophrenic patients. Furthermore, preclinical studies have shown that M1 knock-out mice have enhanced amphetamine-induced activity and increased striatal dopamine levels. Electrophysiology studies have revealed that activation of M1 receptors potentiates NMDA mediated hippocampal activity, modulates activity of medium spiny neurons and increases activity of medial prefrontal cortex neurons. Overall, activation of M1 receptors should modulate dysfunctional dopaminergic and glutamatergic signaling within the underlying neurocircuitry resulting in improvements in the symptoms of schizophrenia.

The clinical effects of Xanomeline and other muscarinic M1 agonist agents were however always associated with adverse effects attributed to their insufficient M1 muscarinic receptor subtype selectivity. The typical observed side effects, including sweating, salivation, gastrointestinal distress and bradycardia have been attributed to the non-specific activation of peripheral M2 and M3 mAChRs. Despite a tremendous effort from a number of companies, the search for highly M1 selective agonists has failed because of the high degree of conservation between muscarinic receptor subtypes at their orthosteric acetylcholine ligand binding sites.

To circumvent the selectivity and safety issues associated with targeting the highly conserved orthosteric ACh site, an alternative approach consists of developing M1 PAMs that act at the less highly conserved allosteric binding sites.

Recently, Merck and Vanderbilt University reported M1 PAMs from different chemical classes exhibiting, as rationalized, a good level of M1 subtype selectivity. Importantly, similar to the preclinical profile of Xanomeline and other unselective M1 agonists, these M1 allosteric agents demonstrated pro-cognitive effects (in scopolamine-induced memory deficit in mice, scopolamine impaired non-human primates and in transgenic AD mice). PQCA and ML169 have been shown to promote non-amyloidogenic APP processing. Electrophysiology studies have shown that M1 PAMs potentiate carbachol-induced activity in the medial prefrontal cortex and medium spiny neurons. Moreover, unlike unselective agonists, M1 PAMs do not appear to produce side effects such as salivation at therapeutic effective doses. Additionally, they are expected to be devoid of liabilities such as receptor desensitization/internalization following chronic dosing previously reported for orthosteric receptor agonists. In summary, the PAM approach, by activating in a truly selective manner M1 receptors, is a highly promising novel strategy to deliver both efficacious and safe therapeutic agents for the treatment of schizophrenia (positive, negative and cognitive symptoms) as well as AD (symptomatic and disease modifying).

Thus, the compounds of the invention, which are muscarinic M1 receptor positive allosteric modulators, are believed to be useful in the treatment of Alzheimer's disease and other diseases mediated by the muscarinic M1 receptor, without side effects.

Therefore, the object of the present invention was to identify compounds that are muscarinic M1 receptor positive allosteric modulators. It has been found that the compounds of formula I are active in this area and they may therefore be used for the treatment of Alzheimer's disease, cognitive impairment, schizophrenia, pain or sleep disorders The present invention relates to compounds of formula I and to their pharmaceutically acceptable salts, to these compounds as pharmaceutically active substances, to the processes for their production, as well as to the use in the treatment or prevention of disorders, relating to muscarinic M1 receptor positive allosteric modulators, and to pharmaceutical compositions containing the compounds of formula I.

The following definitions of the general terms used in the present description apply irrespective of whether the terms in question appear alone or in combination.

As used herein, the term "lower alkyl" denotes a saturated, i.e. aliphatic hydrocarbon group including a straight or branched carbon chain with 1-7 carbon atoms. Examples for "alkyl" are methyl, ethyl, n-propyl, isopropyl, n-butyl, i-butyl, 2-butyl, t-butyl and the like.

As used therein, the term "$C_{4-6}$-cycloalkyl" denotes a saturated carbon ring, containing from 4 to 6 carbon ring atoms, for example cyclobutyl, cyclopentyl or cyclohexyl.

The term "alkoxy" denotes a group —O—R' wherein R' is lower alkyl as defined above.

The term "halogen" denotes chlorine, bromine, fluorine or iodine.

The term "lower alkoxy substituted by halogen" denotes an alkyl group as defined above, wherein at least one hydrogen atoms is replaced by halogen, for example $OCF_3$, $OCH_2F$, $OCH_2CF_3$, $OCH_2CH_2CF_3$, $OCH_2CF_2CF_3$ and the like.

The term "$C_{4-6}$-heterocycloalkyl" denotes a non aromatic heterocyclic ring with 4 to 6 ring atoms, containing at least one 0 atom, for example tetrahydropyran-4-yl, tetrahydropyran-3-yl, oxolan-3-yl, oxetan-3-yl, oxetan-2-yl or tetrahydrofuran-2-yl.

The term "five or six-membered heteroaryl" denotes aromatic rings with 5 or 6 ring atoms, containing at least one N, S or O atom, for example pyrazolyl, imidazolyl, 1,2,4-triazolyl, thiazolyl, 1,2,4-oxadiazolyl or pyridinyl.

The term "pharmaceutically acceptable salt" or "pharmaceutically acceptable acid addition salt" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluenesulfonic acid and the like One embodiment of the present invention are compounds of formula I, wherein A is phenyl and the other substituents are as described above, for example the following compounds:

1-fluoro-N-((3RS,4SR)-3-hydroxytetrahydro-2H-pyran-4-yl)-4-(4-methylbenzyl)-2-naphthamide 4-benzyl-1-fluoro-N-((3RS,4SR)-3-hydroxytetrahydro-2H-pyran-4-yl)-2-naphthamide 4-(4-chlorobenzyl)-1-fluoro-N-((3RS,4SR)-3-hydroxytetrahydro-2H-pyran-4-yl)-2-naphthamide 4-(4-cyanobenzyl)-1-fluoro-N-((3RS,4SR)-3-hydroxytetrahydro-2H-pyran-4-yl)-2-naphthamide 1-fluoro-4-(2-fluoro-4-(1-methyl-1H-pyrazol-4-yl)benzyl)-N-((3RS,4SR)-3-hydroxytetrahydro-2H-pyran-4-yl)-2-naphthamide 1-fluoro-N-((3RS,4SR)-3-hydroxytetrahydro-2H-pyran-4-yl)-4-(4-(trifluoromethoxy)benzyl)-2-naphthamide or 1-fluoro-N-((3RS,4SR)-3-hydroxytetrahydro-2H-pyran-4-yl)-4-(4-(1-methyl-1H-pyrazol-4-yl)benzyl)-2-naphthamide.

One further embodiment of the present invention are compounds of formula I, wherein A is pyridinyl and the other substituents are as described above, for example the following compounds:

4-((6-chloropyridin-3-yl)methyl)-1-fluoro-N-((1SR,2SR)-2-hydroxycyclohexyl)-2-naphthamide 4-((6-chloropyridin-3-yl)methyl)-1-fluoro-N-((3RS,4SR)-3-hydroxytetrahydro-2H-pyran-4-yl)-2-naphthamide 4-((6-chloropyridin-3-yl)methyl)-1-fluoro-N-((1S,2S)-2-hydroxycyclohexyl)-2-naphthamide 4-((6-chloropyridin-3-yl)methyl)-1-fluoro-N-((3S,4S)-4-hydroxytetrahydro-2H-pyran-3-yl)-2-naphthamide 4-((6-chloropyridin-3-yl)methyl)-1-fluoro-N-((1S,2S)-2-hydroxycyclopentyl)-2-naphthamide 4-((6-chloropyridin-3-yl)methyl)-1-fluoro-N-((1S,2R)-2-hydroxycyclopentyl)-2-naphthamide 4-((6-chloropyridin-3-yl)methyl)-1-fluoro-N-((1SR,2SR)-2-hydroxy-2-methylcyclohexyl)-2-naphthamide 4-((6-chloropyridin-3-yl)methyl)-1-fluoro-N-((1SR,2RS)-2-hydroxy-2-methylcyclohexyl)-2-naphthamide 4-((6-chloropyridin-3-yl)methyl)-1-fluoro-N-((1SR,2RS)-2-hydroxycyclohexyl)-2-naphthamide 1-fluoro-N-((1S,2S)-2-hydroxycyclohexyl)-4-((6-(1-methyl-1H-pyrazol-4-yl) pyridin-3-yl)methyl)-2-naphthamide 1-fluoro-N-((3RS,4SR)-3-hydroxytetrahydro-2H-pyran-4-yl)-4-((6-(1-methyl-1H-pyrazol-4-yl)pyridin-3-yl)methyl)-2-naphthamide 1-fluoro-N-[(3S,4R)-3-hydroxytetrahydropyran-4-yl]-4-[[6-(1-methylpyrazol-4-yl)-3-pyridyl]methyl]naphthalene-2-carboxamide 1-fluoro-N-[(3R,4S)-3-hydroxytetrahydropyran-4-yl]-4-[[6-(1-methylpyrazol-4-yl)-3-pyridyl]methyl]naphthalene-2-carboxamide 1-fluoro-N-((3S,4S)-4-hydroxytetrahydro-2H-pyran-3-yl)-4-((6-(1-methyl-1H-pyrazol-4-yl)pyridin-3-yl)methyl)-2-naphthamide 1-fluoro-N-((1SR,2RS)-2-hydroxy-2-methylcyclohexyl)-4-((6-(1-methyl-1H-pyrazol-4-yl)pyridin-3-yl)methyl)-2-naphthamide 1-fluoro-N-((1SR,2SR)-2-hydroxycyclohexyl)-4-((6-methylpyridin-3-yl)methyl)-2-naphthamide 4-((6-cyclopropylpyridin-3-yl)methyl)-1-fluoro-N-((1S,2S)-2-hydroxycyclohexyl)-2-naphthamide 4-[(6-chloropyridin-3-yl)methyl]-1-fluoro-N-[(3S,4R)-3-hydroxyoxan-4-yl]naphthalene-2-carboxamide One embodiment of the invention are further compounds of formula I, wherein A is piperidinyl and the other substituents are as described above, for example the following compound 4-((4-cyano-4-(pyridin-2-yl)piperidin-1-yl)methyl)-1-fluoro-N-((1S,2S)-2-hydroxycyclohexyl)-2-naphthamide The present compounds of formula I and their pharmaceutically acceptable salts can be prepared by methods known in the art, for example, by processes described below, which process comprises a) reacting a compound of formula

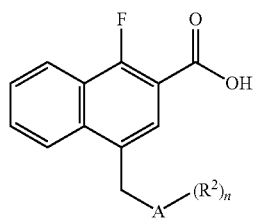

with a compound of formula

   2 in the presence of an activating agent such as BOP (Benzotriazol-1-yloxy)tris(dimethylamino)phosphonium hexafluorophosphate or thionyl chloride to a compound of formula

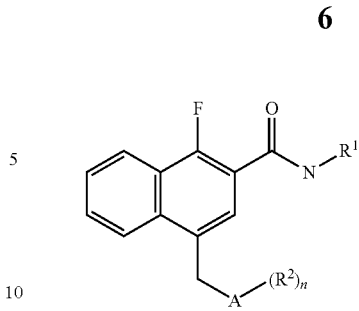   I wherein the substituents are as defined above, and, if desired, converting the compounds obtained into pharmaceutically acceptable acid addition salt.

The compounds of formula I may be prepared in accordance with process variant a) and with the following schemes 1 and 2. Starting materials are commercially available, known in the art or can be prepared by methods known in the art or in analogy thereto.

Insofar as their preparation is not described in the examples, the compounds of formula (I) as well as all intermediate products can be prepared according to analogous methods or according to the methods set forth below.

Scheme 1

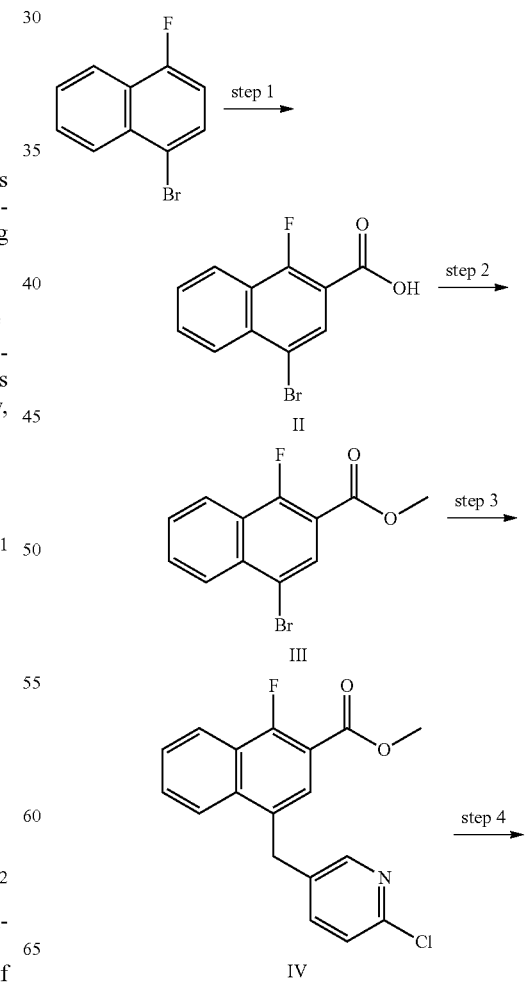

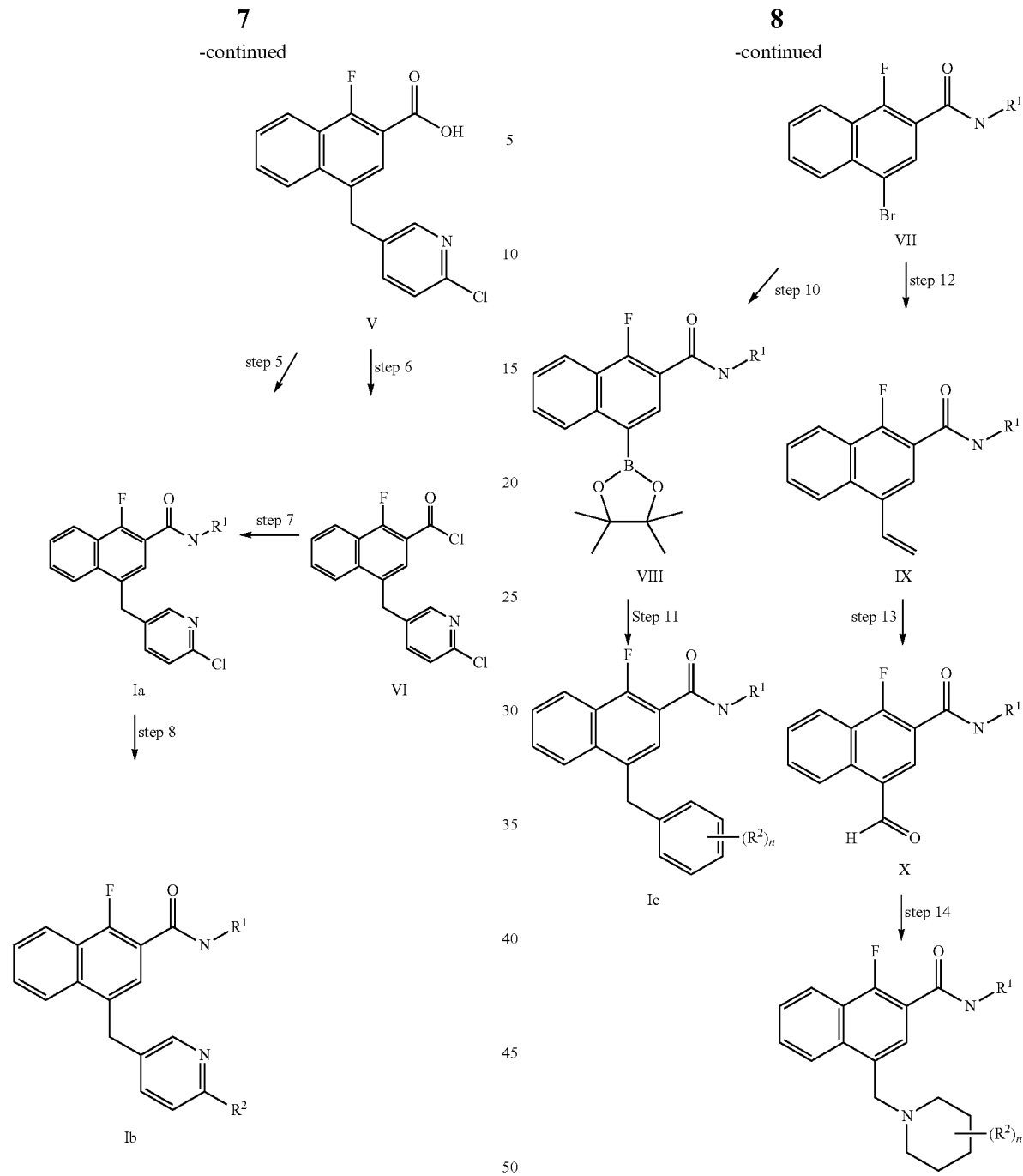

$R^1$ is as described above and $R^2$ is lower alkyl, $C_{4-6}$-cycloalkyl or is a five- or six-membered heteroaryl group, optionally substituted by lower alkyl;

Scheme 2

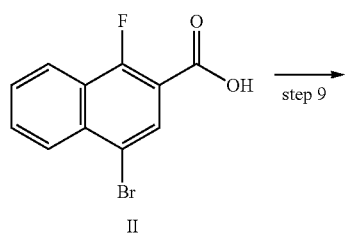

A compound of general formula Ia can be obtained by coupling acid V with an amine $H_2N-R1$ (step 5). Alternatively, it can be obtained by reaction an amine $H_2N-R1$ with acid chloride V (step 7). A compound of general formula Ib is obtained from a compound of general formula Ia by Suzuki reaction with a heteroaryl boronic acid or heteroaryl boronic acid ester or alternatively by reaction with dimethyl zinc or cyclopropyl boronic acid in the presence of a Pd catalyst (step 8). A compound of general formula Ic is obtained by Suzuki reaction of a benzyl halogenide with a boronic acid ester of general formula VIII (step 11). A compound of general formula Id is obtained by reductive amination of an aldehyde X with a substituted piperidine (step 14).

Intermediates II-X are obtained as described below, in analogy to methods described in the literature or by methods know to those skilled in the art.

Isolation and Purification of the Compounds

Isolation and purification of the compounds and intermediates described herein can be effected, if desired, by any suitable separation or purification procedure such as, for example, filtration, extraction, crystallization, column chromatography, thin-layer chromatography, thick-layer chromatography, preparative low or high-pressure liquid chromatography or a combination of these procedures. Specific illustrations of suitable separation and isolation procedures can be had by reference to the preparations and examples herein below. However, other equivalent separation or isolation procedures could, of course, also be used.

Salts of Compounds of Formula I

The compounds of formula I are basic and may be converted to a corresponding acid addition salt. The conversion is accomplished by treatment with at least a stoichiometric amount of an appropriate acid, such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid and the like. Typically, the free base is dissolved in an inert organic solvent such as diethyl ether, ethyl acetate, chloroform, ethanol or methanol and the like, and the acid added in a similar solvent. The temperature is maintained between 0° C. and 50° C. The resulting salt precipitates spontaneously or may be brought out of solution with a less polar solvent.

The acid addition salts of the basic compounds of formula I may be converted to the corresponding free bases by treatment with at least a stoichiometric equivalent of a suitable base such as sodium or potassium hydroxide, potassium carbonate, sodium bicarbonate, ammonia, and the like.

The compounds of formula I and their pharmaceutically usable addition salts possess valuable pharmacological properties. Specifically, it has been found that the compounds of the present invention have an activity as neurogenic agents.

The compounds were investigated in accordance with the test given hereinafter.

M1 PAM Assay

The assay is designed to select compounds that possess modulator activity at the acetylcholine muscarinic receptor expressed in CHO cells by measuring the intracellular calcium with a Fluorometric Imaging Plate Reader System (FLIPR, Molecular Devices). The assay study the effect of several concentrations of test compounds on basal or acetylcholine-stimulated $Ca^{2+}$ levels using FLIPR.

CHO human M1 are plated the day before the experiments at $2 \times 10^5$ cells/ml in PDL BioCoat 96 well black/clear plate (Becton 35 4640). The cells are grown at 37° C. and 5% $CO_2$ in the following medium: F12 Nut Mix (Gibco 21765), 10% FCS heat inactivated (GIBCO 16000-044), 1% Pen Strep (Gibco, 15140) and 200 μg/ml Geneticin (Gibco 11811). On the day of the experiment, the medium was removed and replaced by 100 μl of dye loading buffer containing Hanks Balanced Salt solution (HBSS, 14065-049, Gibco) with 20 mM HEPES (Gibco 15630-056), 2 mM Probenicid (Sigma P8761), 2 mM Fluo-4AM ester (Molecular Probes F-14202), 10% Pluronic acid Molecular Probes P-3000) pH=7.4 and incubated at 37° C. After 60 minutes extracellular dye was removed and the cells were washed five times with FLIPR buffer containing HBSS (Gibco 14065-049) with 20 mM HEPES (Gibco, 15630-056), 2 mM Probenicid (Sigma P8761) pre-warmed at 37° C. using and Ebml cell washer leaving 100 μl of FLIPR buffer in each well. The cell plate and the diluted compounds (1% DMSO final concentration) are placed on the platform of the FLIPR and the door closed. A signal test to check background fluorescence and basal fluorescence signal is performed. Laser intensity is adjusted if necessary. Two minutes preincubation with the diluted test compounds is provide to determine any agonist activity on the M1 receptor by comparison to 30 nM Acetylcholine control. In order to determine any modulator activity the diluted compounds were added to cells and after two minutes preincubation, the $EC_{20}$ of acetylcholine is added followed by another two minutes preincubation before the measurement of intracellular $Ca^{2+}$ with a FLIPR (Molecular Devices).

| Table with activity data | |
| --- | --- |
| Example | hM1 $EC_{50}$/ rat M1 $EC_{50}$ (nM) |
| 1 | 159/137 |
| 2 | 53/118 |
| 3 | 84/101 |
| 4 | 428 |
| 5 | 363/968 |
| 6 | 575 |
| 7 | 561 |
| 8 | 524 |
| 9 | 539 |
| 10 | 154/221 |
| 11 | 197/356 |
| 12 | 152/273 |
| 13 | 67/71 |
| 14 | 14/14 |
| 15 | 541 |
| 16 | 11/20 |
| 17 | 10/14 |
| 18 | 3/6 |
| 19 | 65/97 |
| 20 | 2/2 |
| 21 | 33/48 |
| 22 | 20/41 |
| 23 | 213/490 |
| 24 | 230/347 |
| 25 | 27/52 |
| 26 | 258/345 |

The 26 compounds of formula (I) and pharmaceutically acceptable salts thereof can be used as medicaments, e.g. in the form of pharmaceutical preparations. The pharmaceutical preparations can be administered orally, e.g. in the form of tablets, coated tablets, dragées, hard and soft gelantine capsules, solutions, emulsions or suspensions. However, the administration can also be effected rectally, e.g. in the form of suppositories, or parenterally, e.g. in the form of injection solutions.

The compounds of formula (I) and pharmaceutically acceptable salts thereof can be processed with pharmaceutically inert, inorganic or organic carriers for the production of pharmaceutical preparations. Lactose, corn starch or derivatives thereof, talc, stearic acid or its salts and the like can be used, for example, as such carriers for tablets, coated tablets, dragées and hard gelantine capsules. Suitable carriers for soft gelantine capsules are, for example, vegetable oils, waxes, fats, semi-solid and liquid polyols and the like; depending on the nature of the active substance no carriers are, however, usually required in the case of soft gelantine capsules. Suitable carriers for the production of solutions and syrups are, for example, water, polyols, sucrose, invert sugar, glucose and the like. Adjuvants, such as alcohols, polyols, glycerol, vegetable oils and the like, can be used for aqueous injection solutions of water-soluble salts of compounds of formula (I), but as a rule are not necessary. Suitable carriers for suppositories are, for example, natural or hardened oils, waxes, fats, semi-liquid or liquid polyols and the like.

In addition, the pharmaceutical preparations can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

As mentioned earlier, medicaments containing a compound of formula (I) or pharmaceutically acceptable salts thereof and a therapeutically inert excipient are also an object of the present invention, as is a process for the production of such medicaments which comprises bringing one or more compounds of formula (I) or pharmaceutically acceptable salts thereof and, if desired, one or more other therapeutically valuable substances into a galenical dosage form together with one or more therapeutically inert carriers.

As further mentioned earlier, the use of the compounds of formula (I) for the preparation of medicaments useful in the prevention and/or the treatment of the above recited diseases is also an object of the present invention.

The dosage can vary within wide limits and will, of course, be fitted to the individual requirements in each particular case. In general, the effective dosage for oral or parenteral administration is between 0.01-20 mg/kg/day, with a dosage of 0.1-10 mg/kg/day being preferred for all of the indications described. The daily dosage for an adult human being weighing 70 kg accordingly lies between 0.7-1400 mg per day, preferably between 7 and 700 mg per day.

Pharmaceutical Compositions Comprising Compounds of the Invention

| | Tablet Formulation (Wet Granulation) | | | | |
|---|---|---|---|---|---|
| | | mg/tablet | | | |
| Item | Ingredients | 5 mg | 25 mg | 100 mg | 500 mg |
| 1. | Compound of formula I | 5 | 25 | 100 | 500 |
| 2. | Lactose Anhydrous DTG | 125 | 105 | 30 | 150 |
| 3. | Sta-Rx 1500 | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure
1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

| | Capsule Formulation | | | | |
|---|---|---|---|---|---|
| | | mg/capsule | | | |
| Item | Ingredients | 5 mg | 25 mg | 100 mg | 500 mg |
| 1. | Compound of formula I | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure
1. Mix items 1, 2 and 3 in a suitable mixer for 30 minutes.
2. Add items 4 and 5 and mix for 3 minutes.
3. Fill into a suitable capsule.

EXPERIMENTAL PART

Preparation of Intermediates

Example A.1

4-[(6-Chloro-3-pyridyl)methyl]-1-fluoro-naphthalene-2-carboxylic acid

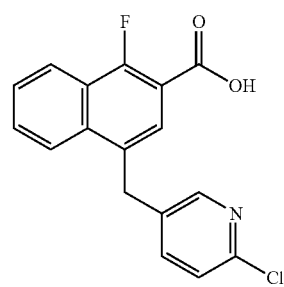 [SMILES: O=C(O)c1cc(Cc2ccc(Cl)nc2)c2ccccc2c1F]

Step 1: 4-Bromo-1-fluoro-2-naphthoic acid

A solution of 2,2,6,6-tetramethylpiperidine (6.85 g, 8.25 ml, 48.0 mmol) in THF (70.0 ml) was cooled to −78° C. under nitrogen atmosphere and n-butyl lithium (29.9 ml, 47.9 mmol) was added dropwise to the reaction mixture. The reaction was stirred at −78° C. for 30 min and a solution of 1-bromo-4-fluoronaphthalene (10 g, 43.5 mmol) in THF (20 ml) was added dropwise at −78° C. The mixture was stirred for 1 h and solid $CO_2$ was added at the same temperature. The reaction was stirred for 2 h and treated with 20% aqueous ammonium chloride solution. The mixture was allowed to warm to room temperature, was acidified by a solution of HCl 1N and was diluted with EtOAc. The aqueous layer was extracted two times with EtOAc. The combined organic layers were dried over $Na_2SO_4$, filtered and the solvent was removed into vacuo. The precipitate was taken up in $CH_2Cl_2$ and filtered to provide the title compound (8.6 g, 74%) as white solid. MS (m/e): 267.2, 269.2 $(M+H)^+$

Step 2: Methyl 4-bromo-1-fluoro-2-naphthoate

To a suspension of 4-bromo-1-fluoro-2-naphthoic acid (8.68 g, 32.3 mmol) in dichloromethane (97 ml) were added a few drops of N,N-dimethylformamide. Under nitrogen atmosphere at room temperature, oxalyl chloride (25.1 g, 16.9 ml, 194 mmol) was added dropwise. The mixture reaction was heated at 40° C. for 3 h. The solvent was removed in vacuo. The crude material was quenched with MeOH and stirred for 1 h. The precipitate obtained was filtered and dried to give the title compound (8.35 g, 91%) as white powder. MS (m/e): 330.4 $(M+H)^+$

Step 3: Methyl 4-((6-chloropyridin-3-yl)methyl)-1-fluoro-2-naphthoate

A solution of methyl 4-bromo-1-fluoro-2-naphthoate (3.7 g, 13.1 mmol) and bis(tri-tert-butylphosphine)palladium (667 mg, 1.28 mmol) in THF (48 ml) under nitrogen atmosphere was cooled to −60° C. A ((6-chloropyridin-3-yl)methyl)zinc(II) chloride solution (0.5M in THF; 39.2 ml, 19.6 mmol) was added dropwise at −60° C. The mixture was stirred at −60° C. for 1 h. Another portion of ((6-chloropyridin-3-yl)methyl)zinc(II) chloride solution (0.5M in THF; 39.2 ml, 19.6 mmol) was added dropwise. The mixture was stirred at −60° C. for 30 min, then allowed to warm to room temperature and stirred for 1 h. The mixture was quenched by dropwise addition of a 20% $NH_4Cl$ solution. The suspension was diluted with EtOAc. The aqueous layer was extracted two times with EtOAc. The combined organic layers were dried over Na2SO4, filtered and concentrated in vacuo. The yellow-brown precipitate formed when $CH_2Cl_2$ was added was filtered and the mother liquor was concentrated leaving the crude product as orange oil which was purified by silica gel chromatography using an EtOAc/heptane gradient as eluent. The product-containing fractions were combined and concentrated. The oily solid thus obtained was triturated with diethyl ether, filtered and dried to provide the title compound (1.6 g, 37%) as light yellow solid. MS (m/e): 330.4 $(M+H)^+$

Step 4: 4-[(6-Chloro-3-pyridyl)methyl]-1-fluoro-naphthalene-2-carboxylic acid To a solution of methyl 4-((6-chloropyridin-3-yl)methyl)-1-fluoro-2-naphthoate (1.6 g, 4.85 mmol) in THF (13 ml), methanol (6.5 ml) and water (6.5 ml) was added lithium hydroxide monohydrate (750 mg, 17.9 mmol). The mixture was stirred at room temperature for 2 hours and cooled in an ice-bath, then brought to pH 1 by the dropwise addition of HCl 5N (3 ml). The solvent was removed in vacuo. The residue was stirred in water. The solid was filtered and dried to obtain the title compound (1.47 g, 96%) as white crystals. MS (m/e): 316.4 $(M+H)^+$

Example A.2

4-((6-Chloropyridin-3-yl)methyl)-1-fluoro-2-naphthoyl chloride

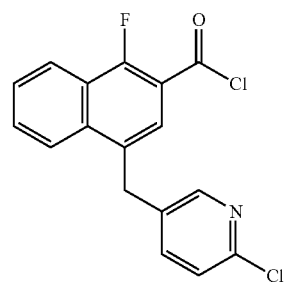 [SMILES: O=C(Cl)c1cc(Cc2ccc(Cl)nc2)c2ccccc2c1F]

To a suspension of 4-((6-chloropyridin-3-yl)methyl)-1-fluoro-2-naphthoic acid (example A.1; 1.27 g, 4.02 mmol) in dichloromethane (12 ml) was added one drop of DMF. Then, oxalyl chloride (3.13 g, 2.11 ml, 24.1 mmol) was added dropwise. The mixture was heated to 40° C. for 1 h. Another portion of oxalyl chloride (620 mg, 419 μl, 4.79 mmol) was added dropwise. The mixture was stirred at 40° C. for 1.5 h. The mixture was concentrated and dried to provide the title compound (1.46 g, quant.; 92% purity) as light yellow solid.

Example A.3

1-Fluoro-N-((3RS,4SR)-3-hydroxytetrahydro-2H-pyran-4-yl)-4-(4,4,5,5-tetramethyl-1,3,2-dioxaborolan-2-yl)-2-naphthamide

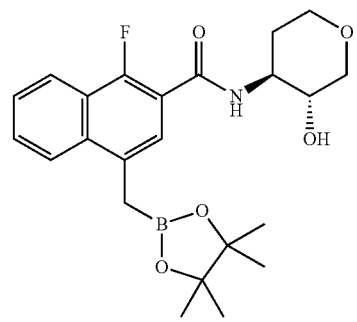 [SMILES: CC1(C)OB(Cc2cc(C(=O)N[C@H]3CCOC[C@@H]3O)c(F)c3ccccc23)OC1(C)C]

Step 1: 4-Bromo-1-fluoro-N-((3RS,4SR)-3-hydroxytetrahydro-2H-pyran-4-yl)-2-naphthamide To a suspension of 4-bromo-1-fluoro-2-naphthoic acid (example A.1, step 1; 400 mg, 1.49 mmol) in dichloromethane (8.00 ml) were added (3SR,4RS)-4-aminotetrahydro-2H-pyran-3-ol hydrochloride (example B.1; 228 mg, 1.49 mmol), BOP (874 mg, 1.98 mmol) and triethylamine (451 mg, 621 µl, 4.46 mmol). The solution was stirred at room temperature for 17 hours. The solvent was removed in vacuo. The solid was stirred in water, filtered and dried, then taken up in EtOAc (5 ml), filtered and dried to give the title compound (600 mg, 99%, 90% purity) as white solid. MS (m/e): 366.3 (M−H); MS (m/e): 366.3; 368.3 (M−H)⁻

Step 2: 1-Fluoro-N-((3RS,4SR)-3-hydroxytetrahydro-2H-pyran-4-yl)-4-(4,4,5,5-tetramethyl-1,3,2-dioxaborolan-2-yl)-2-naphthamide A mixture of 4-bromo-1-fluoro-N-((3RS,4SR)-3-hydroxytetrahydro-2H-pyran-4-yl)-2-naphthamide (300 mg, 733 µmol), 4,4,4',4',5,5,5',5'-octamethyl-2,2'-bi(1,3,2-dioxaborolane) (285 mg, 1.1 mmol), $Pd_2(dba)_3$ (34.6 mg, 36.7 µmol), tribasic potassium phosphate (353 mg, 1.61 mmol) and tricyclohexylphosphine (30.8 mg, 110 µmol) in dioxane (6 ml) was heated in an 80° C. oil bath for 12 hours. The mixture was cooled to room temperature, diluted with ethyl acetate and washed with water. The aqueous layer was back-extracted once with ethyl acetate. The combined organic fractions were dried over $Na_2SO_4$, filtered and concentrated. The crude product was purified by silica gel chromatography using a heptane/EtOAc gradient as eluent to obtain the title compound (240 mg, 79%) as white solid. MS (m/e): 416.5 (M+H)⁺

Example B.1

(3R,4S)-4-Aminotetrahydropyran-3-ol hydrochloride

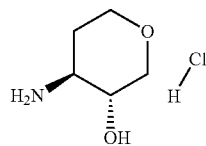

Step 1: Methanesulfonic acid tetrahydro-pyran-4-yl ester

To a solution of tetrahydro-2H-pyran-4-ol (25 g, 245 mmol) and triethyl amine (40.1 ml, 294 mmol) in $CH_2Cl_2$ (500 ml) at 0° C. was added dropwise methanesulfonylchloride (20.7 ml, 269 mmol) over a period of 40 min, keeping the temperature between 0°-4° C. The reaction mixture was then allowed to stir at 0° C. for 1 hr. The cooling bath was removed and the mixture was stirred for another 90 mins at 25° C. The mixture was washed with water (2×125 ml), dried over anhydrous $Na_2SO_4$, filtered and concentrated under vacuum to get methanesulfonic acid tetrahydro-pyran-4-yl ester (38 g, 86%; crude) as liquid that was used in the next step without any further purification.

Step 2: 3,6-Dihydro-2H-pyran

A mixture of tetrahydro-2H-pyran-4-yl methanesulfonate (20 g, 111 mmol) and DBU (18.8 ml, 125.6 mmol) was distilled under normal atmospheric pressure. The fraction at 90°-96° C. was 6-dihydro-2H-pyran (6 g, 64%) as colourless liquid.

Step 3: (1SR, 6RS)-3,7-Dioxa-bicyclo[4.1.0]heptane

To a solution of 3,6-dihydro-2H-pyran (6 g, 71.4 mmol,) in $CH_2Cl_2$ (300 ml) was added 3-chloroperbenzoic acid (25 g, 107.1 mmol) portionwise at 25° C., and stirred at that temperature for 21 hrs. The resultant white suspension was diluted with water (250 ml) and then with aqueous solution of $Na_2SO_3$. The mixture was stirred at 25° C. for 10 min, then basified by addition of saturated aqueous solution of $NaHCO_3$. The organic layer was separated, and the aqueous layer was re-extracted with $CH_2Cl_2$. The combined organic layers were washed with saturated aqueous solution of $NaHCO_3$ (100 ml), and brine (80 ml), dried over anhydrous $Na_2SO_4$, filtered and concentrated in vacuo to afford the title compound (5 g, 70%; crude) as yellow liquid.

Step 4: (3SR,4RS)-4-Azidotetrahydropyran-3-ol

To a solution of (1SR,6RS)-3,7-dioxabicyclo[4.1.0]heptane (5 g, 49.9 mmol) in MeOH (50 ml) were added sodium azide (24.3 g, 374.6 mmol), ammonium chloride (20 g, 374.6 mmol) and water (5 ml), and the resultant mixture was stirred at 25° C. for 19 hrs, and then at 70° C. for 2 hrs. The mixture was cooled 0° C., and the precipitated solid was filtered and washed with methanol. The filtrate was concentrated in vacuo. Resultant residue was taken in ethyl acetate, and filtered. Removal of the filtrate in vacuo yielded the title compound (5 g, 70%; crude) as yellow liquid.

Step 5: (3SR,4RS)-4-Aminotetrahydropyran-3-ol

To a solution of (3SR,4RS)-4-azidotetrahydropyran-3-ol (5 g, 35 mmol) in ethyl acetate (50 ml), was added $Pd(OH)_2$ on charcoal (1.25 g, 1.4 mmol). The mixture was purged with argon, and then allowed to stir under a balloon pressure of hydrogen for 21 hrs at 25° C. Removal of the catalyst by filtration followed by evaporation of the filtrate in vacuo afforded the title compound (4 g, crude).

Step 6: (3S,4R)-3-Hydroxy-tetrahydro-pyran-4-yl)-carbamic acid benzyl ester and ((3R,4S)-3-hydroxy-tetrahydro-pyran-4-yl)-carbamic acid benzyl ester To a solution of (3SR,4RS)-4-aminotetrahydropyran-3-ol (10 g, 85.4 mmol) and $Et_3N$ (23.6 ml, 170.9 mmol) in CH₂Cl₂ (100 ml) was added benzyl chloroformate (9.8 ml, 59.9 mmol) dropwise at 0° C. After completion of addition, the mixture was stirred at 25° C. for 2 hrs. The mixture was washed with water (60 ml). The aqueous layer was re-extracted with CH₂Cl₂. The combined organic layers were dried over anhydrous Na₂SO₄, filtered and concentrated in vacuo to get the mixture the two regioisomeric pairs of enantiomers (16 g). This crude product was purified by silica gel chromatography using 45% EtOAc in hexane as eluent to get the pair of enantiomers with the desired regioisomery as white solid (4.5 g, 21%). This enantiomeric mixture was subject to chiral separation by SFC to afford (3S,4R)-3-hydroxy-tetrahydro-pyran-4-yl)-carbamic acid benzyl ester (1.7 g, 8%) and ((3R,4S)-3-hydroxy-tetrahydro-pyran-4-yl)-carbamic acid benzyl ester (1.7 g, 8%) both as white solid.

Step 7: (3R,4S)-4-Amino-tetrahydro-pyran-3-ol hydrochloride

To a solution of ((3R,4S)-3-hydroxy-tetrahydro-pyran-4-yl)-carbamic acid benzyl ester (1.1 g, 4.4 mmol) in MeOH (50 ml) was added 10% palladium on charcoal (140 mg, 0.13 mmol), and stirred the reaction mixture under hydrogen atmosphere for 1 hr. The catalyst was filtered off. The filtrate was acidified with 1.25 M HCl in MeOH and concentrated in vacuo to get (3R,4S)-4-amino-tetrahydro-pyran-3-ol hydrochloride as off white solid (500 mg, 97%).

DESCRIPTION OF EXAMPLES

Example 1

4-((6-Chloropyridin-3-yl)methyl)-1-fluoro-N-((1SR,2SR)-2-hydroxycyclohexyl)-2-naphthamide

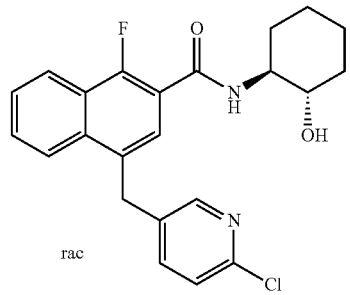

To a suspension of 4-((6-chloropyridin-3-yl)methyl)-1-fluoro-2-naphthoic acid (example A.1; 147.2 mg, 466 μmol) in dichloromethane (3 ml) were added trans-2-aminocyclohexanol hydrochloride (89.0 mg, 581 μmol), BOP (282.1 mg, 625 μmol) and triethylamine (189 mg, 260 μl, 1.86 mmol). The solution was stirred at room temperature for 22 h, then diluted with dichloromethane and washed twice with water. The aqueous layer was back-extracted once with dichloromethane. The combined organic layers were dried over Na₂SO₄, filtered and concentrated. The crude product was purified by silica gel column chromatography using a heptane/EtOAc gradient as eluent to provide the title compound (165 mg, 86%) as white solid.

MS (m/e): 413.5 (M+H)

In analogy to example 1, examples 2 and 3 of the following table were prepared by coupling 4-((6-chloropyridin-3-yl)methyl)-1-fluoro-2-naphthoic acid (example A.1) with an amine.

| Exp. No. | Structure | Systematic Name | Starting materials | MW found (MH⁺) |
|---|---|---|---|---|
| 2 | 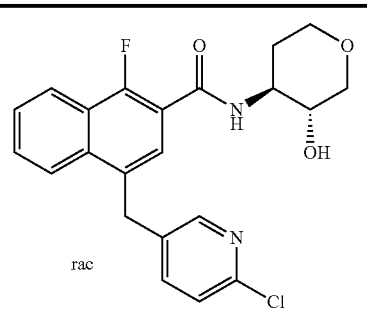 | 4-((6-chloropyridin-3-yl)methyl)-1-fluoro-N-((3RS,4SR)-3-hydroxytetrahydro-2H-pyran-4-yl)-2-naphthamide | (3RS,4SR)-4-aminotetrahydro-2H-pyran-3-ol (CAS 215940-92-4) | 415.5 |
| 3 | 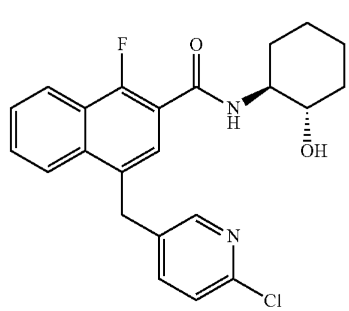 [SMILES: O=C(N[C@H]1CCCC[C@@H]1O)c1cc(Cc2ccc(Cl)nc2)c2ccccc2c1F] | 4-((6-chloropydridin-3-yl)methyl)-1-fluoro-N-((1S,2S)-2-hydroxycyclohexyl)-2-naphthamide | (1S,2S)-2-aminocyclohexanol hydrochloride (CAS 74111-21-0) | 413.4 |

Example 4

4-((6-Chloropyridin-3-yl)methyl)-1-fluoro-N-((3S,4S)-4-hydroxytetrahydro-2H-pyran-3-yl)-2-naphthamide

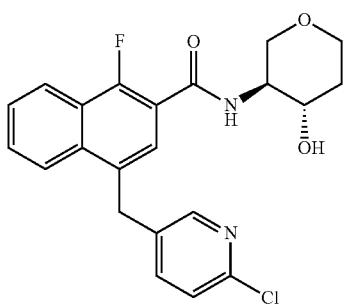 [SMILES: O=C(N[C@H]1COCC[C@@H]1O)c1cc(Cc2ccc(Cl)nc2)c2ccccc2c1F]

To a solution of (3S,4S)-3-aminotetrahydro-2H-pyran-4-ol (CAS 1240390-32-2; 19.3 mg, 165 μmol) and triethylamine (60.6 mg, 83.3 μl, 598 μmol) in dichloromethane (2.0 ml) was added 4-((6-chloropyridin-3-yl)methyl)-1-fluoro-2-naphthoyl chloride (example A.2; 50 mg, 150 μmol). The mixture was stirred at room temperature for 2 hours. The solvent was removed in vacuo. The residue was stirred in water. The solid was filtered, washed with water and dissolved in dichloromethane. The solution was dried over $Na_2SO_4$, filtered and concentrated to give a light yellow solid which was triturated in ether, filtered, washed with ether and hexane and dried providing the title compound (45 mg, 73%) as white solid. MS (m/e): 415.4 $(M+H)^+$ In analogy to example 4, compounds 5 to 9 of the following table were prepared from 4-((6-chloropyridin-3-yl)methyl)-1-fluoro-2-naphthoyl chloride (example A.2) and an amine:

| Exp. No. | Structure | Systematic Name | Starting materials | MW found $(MH^+)$ |
|---|---|---|---|---|
| 5 | 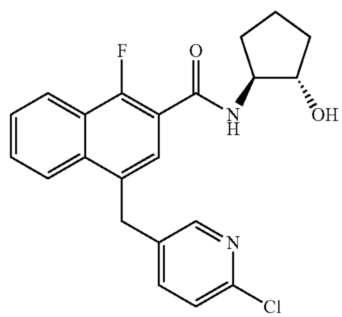 [SMILES: O=C(N[C@H]1CCC[C@@H]1O)c1cc(Cc2ccc(Cl)nc2)c2ccccc2c1F] | 4-((6-chloropyridin-3-yl)methyl)-1-fluoro-N-((1S,2S)-2-hydroxycyclopentyl)-2-naphthamide | (1S,2S)-2-aminocyclopentanol hydrochloride | 399.4 |
| 6 | 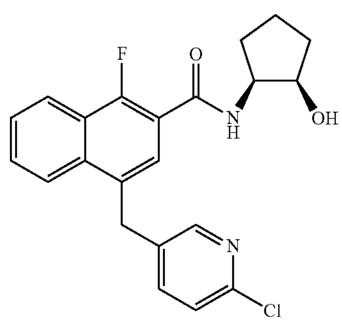 [SMILES: O=C(N[C@H]1CCC[C@H]1O)c1cc(Cc2ccc(Cl)nc2)c2ccccc2c1F] | 4-((6-chloropydridin-3-yl)methyl)-1-fluoro-N-((1S,2R)-2-hydroxycyclopentyl)-2-naphthamide | (1R,2S)-2-aminocyclopentanol hydrochloride | 399.4 |
| 7 | 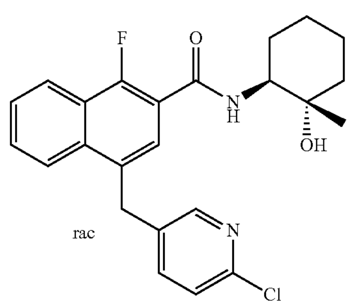 [SMILES: C[C@]1(O)CCCC[C@@H]1NC(=O)c1cc(Cc2ccc(Cl)nc2)c2ccccc2c1F] | 4-((6-chloropyridin-3-yl)methyl)-1-fluoro-N-((1SR,2SR)-2-hydroxy-2-methylcyclohexyl)-2-naphthamide | (1SR,2SR)-2-amino-1-methylcyclohexanol hydrochloride (CAS 837733-18-1) | 427.4 |

| Exp. No. | Structure | Systematic Name | Starting materials | MW found (MH+) |
|---|---|---|---|---|
| 8 | 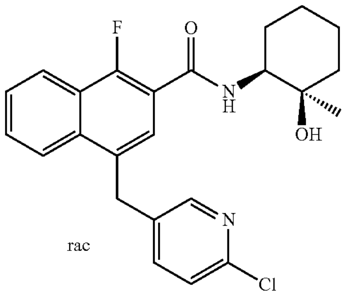 [SMILES: C[C@@]1(O)CCCC[C@@H]1NC(=O)c1cc(Cc2ccc(Cl)nc2)c2ccccc2c1F] | 4-((6-chloropyridin-3-yl)methyl)-1-fluoro-N-((1SR,2RS)-2-hydroxy-2-methylcyclohexyl)-2-naphthamide | (1RS,2SR)-2-amino-1-methylcyclohexanol hydrochloride (CAS 837377-17-0) | 427.4 |
| 9 | 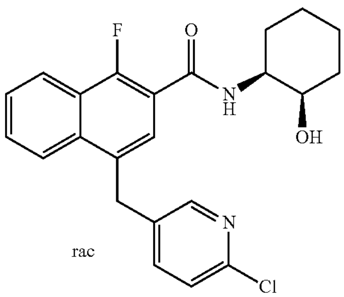 [SMILES: O=C(N[C@H]1CCCC[C@H]1O)c1cc(Cc2ccc(Cl)nc2)c2ccccc2c1F] | 4-((6-chloropyridin-3-yl)methyl)-1-fluoro-N-((1SR,2RS)-2-hydroxycyclohexyl)-2-naphthamide | (1RS,2SR)-2-aminocyclohexanol hydrochloride | 413.4 |

Example 10

1-Fluoro-N-((3RS,4SR)-3-hydroxytetrahydro-2H-pyran-4-yl)-4-(4-methylbenzyl)-2-naphthamide

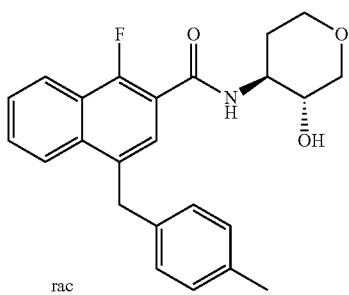 [SMILES: Cc1ccc(Cc2cc(C(=O)N[C@H]3CCOC[C@@H]3O)c(F)c3ccccc23)cc1]

A mixture of 1-fluoro-N-((3RS,4SR)-3-hydroxytetrahydro-2H-pyran-4-yl)-4-(4,4,5,5-tetramethyl-1,3,2-dioxaborolan-2-yl)-2-naphthamide (example A.3; 30 mg, 72.2 µmol), Pd$_2$(dba)$_3$ (3.31 mg, 3.61 µmol), tricyclohexylphosphine (3.04 mg, 10.8 µmol), tribasic potassium phosphate (35.3 mg, 166 µmol) and 1-(chloromethyl)-4-methylbenzene (13.2 mg, 12.4 µl, 93.9 µmol) in dioxane (500 µl) and water (200 µl) was stirred at 140° C. under microwave irradiation for 30 minutes. The mixture was diluted with ethyl acetate and water. The aqueous layer was separated and extracted twice with ethyl acetate. The combined organic fractions were dried over Na$_2$SO$_4$, filtered and concentrated. The crude product was purified by silica gel chromatography using a heptane/EtOAc gradient as eluent to obtain the title compound (19 mg, 67%) as off-white solid. MS (m/e): 394.5 (M+H)

In analogy to Example 10, compounds 11 to 16 of the following table were prepared by reaction of 1-fluoro-N-((3RS,4SR)-3-hydroxytetrahydro-2H-pyran-4-yl)-4-(4,4,5,5-tetramethyl-1,3,2-dioxaborolan-2-yl)-2-naphthamide (example A.3) with a benzyl chloride reagent.

| Expl. No. | Structure | Systematic Name | Starting materials | MW found (MH+) |
|---|---|---|---|---|
| 11 | 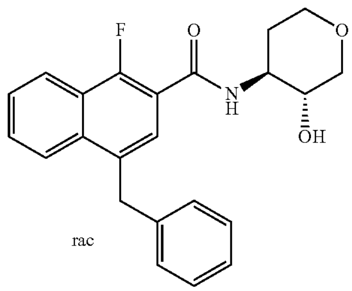 [SMILES: O=C(N[C@H]1CCOC[C@@H]1O)c1cc(Cc2ccccc2)c2ccccc2c1F] | 4-benzyl-1-fluoro-N-((3RS,4SR)-3-hydroxytetrahydro-2H-pyran-4-yl)-2-naphthamide | (chloromethyl)-benzene | 380.4 |

| Expl. No. | Structure | Systematic Name | Starting materials | MW found (MH⁺) |
|---|---|---|---|---|
| 12 | 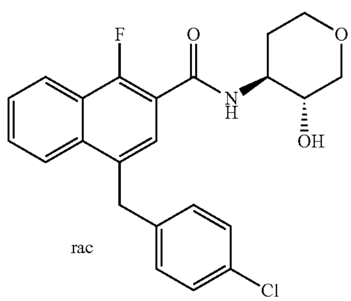 [SMILES: O=C(N[C@H]1CCOC[C@@H]1O)c1cc(Cc2ccc(Cl)cc2)c2ccccc2c1F] | 4-(4-chlorobenzyl)-1-fluoro-N-((3RS,4SR)-3-hydroxytetrahydro-2H-pyran-4-yl)-2-naphthamide | 1-chloro-4-(chloromethyl)-benzene | 414.5 |
| 13 | 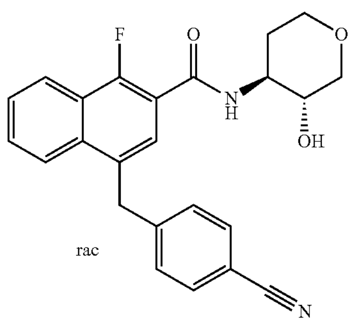 [SMILES: N#Cc1ccc(Cc2cc(C(=O)N[C@H]3CCOC[C@@H]3O)c(F)c3ccccc23)cc1] | 4-(4-cyanobenzyl)-1-fluoro-N-((3RS,4SR)-3-hydroxytetrahydro-2H-pyran-4-yl)-2-naphthamide | 4-(chloromethyl)benzonitrile | 405.5 |
| 14 | 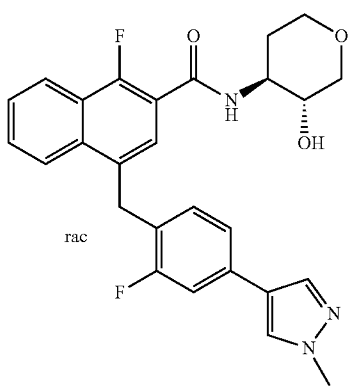 [SMILES: Cn1cc(-c2ccc(Cc3cc(C(=O)N[C@H]4CCOC[C@@H]4O)c(F)c4ccccc34)c(F)c2)cn1] | 1-fluoro-4-(2-fluoro-4-(1-methyl-1H-pyrazol-4-yl)benzyl)-N-((3RS,4SR)-3-hydroxytetrahydro-2H-pyran-4-yl)-2-naphthamide | 4-(4-(chloromethyl)-3-fluorophenyl)-1-methyl-1H-pyrazole (CAS 1392081-37-6) | 478.3 |
| 15 | 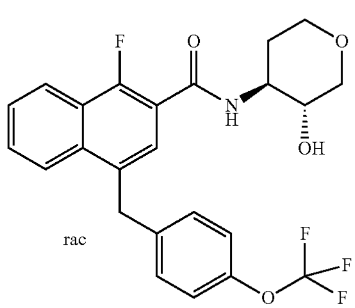 [SMILES: O=C(N[C@H]1CCOC[C@@H]1O)c1cc(Cc2ccc(OC(F)(F)F)cc2)c2ccccc2c1F] | 1-fluoro-N-((3RS,4SR)-3-hydroxytetrahydro-2H-pyran-4-yl)-4-(4-(trifluoromethoxy)benzyl)-2-naphthamide | 1-(chloromethyl)-4-(trifluoromethoxy)-benzene | 464.4 |

| Expl. No. | Structure | Systematic Name | Starting materials | MW found (MH+) |
|---|---|---|---|---|
| 16 | 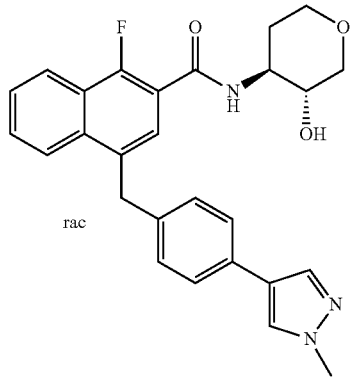 [SMILES: Cn1cc(-c2ccc(Cc3cc(C(=O)N[C@H]4CCOC[C@@H]4O)c(F)c4ccccc34)cc2)cn1] | 1-fluoro-N-((3RS,4SR)-3-hydroxytetrahydro-2H-pyran-4-yl)-4-(4-(1-methyl-1H-pyrazol-4-yl)benzyl)-2-naphthamide | 4-(4-(chloromethyl)-phenyl)-1-methyl-1H-pyrazole | 460.4 |

Example 17

1-Fluoro-N-((1S,2S)-2-hydroxycyclohexyl)-4-((6-(1-methyl-1H-pyrazol-4-yl) pyridin-3-yl)methyl)-2-naphthamide

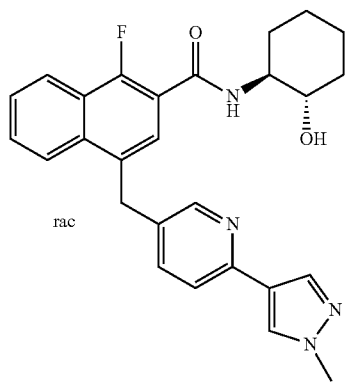 [SMILES: Cn1cc(-c2ccc(Cc3cc(C(=O)N[C@H]4CCCC[C@@H]4O)c(F)c4ccccc34)cn2)cn1]

To a solution of tribasic potassium phosphate (77.7 mg, 366 μmol) in water (280 μl) were added 4-((6-chloropyridin-3-yl)methyl)-1-fluoro-N-((1S,2S)-2-hydroxycyclohexyl)-2-naphthamide (58.4 mg, 141 μmol), 1-methyl-4-(4,4,5,5-tetramethyl-1,3,2-dioxaborolan-2-yl)-1H-pyrazole (36.6 mg, 171 μmol), $Pd_2(dba)_3$ (3.2 mg, 3.39 μmol) and tricyclohexylphosphine (3.8 mg, 13.1 μmol) in dioxane (0.7 ml). The mixture was heated to 140° C. in a microwave reactor for 30 min, then diluted with EtOAc and water. The organic layer was separated and the aqueous layer was extracted once with EtOAc. The combined organic layers were dried over $Na_2SO_4$, filtered and concentrated. The crude material was purified by silica gel chromatography using a heptane/EtOAc gradient to obtain the title compound (39 mg, 60%) as white powder. MS (m/e): 459.5 (M+H)

In analogy to example 17, compounds 18 to 21 of the following table were prepared by Suzuki coupling between the indicated starting material and 1-methyl-4-(4,4,5,5-tetramethyl-1,3,2-dioxaborolan-2-yl)-1H-pyrazole.

| Exp. No. | Structure | Systematic Name | Starting materials | MW found (MH+) |
|---|---|---|---|---|
| 18 | 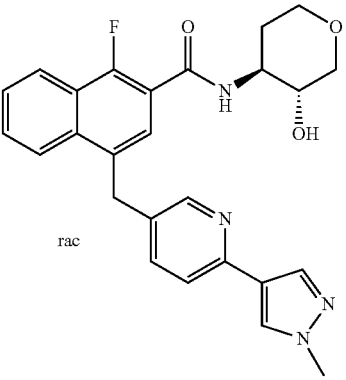 [SMILES: Cn1cc(-c2ccc(Cc3cc(C(=O)N[C@H]4CCOC[C@@H]4O)c(F)c4ccccc34)cn2)cn1] | 1-fluoro-N-((3RS,4SR)-3-hydroxytetrahydro-2H-pyran-4-yl)-4-((6-(1-methyl-1H-pyrazol-4-yl)pyridin-3-yl)methyl)-2-naphthamide | 4-((6-chloropyridin-3-yl)methyl)-1-fluoro-N-((3RS,4SR)-3-hydroxytetrahydro-2H-pyran-4-yl)-2-naphthamide (example 2) | 461.6 |

| Exp. No. | Structure | Systematic Name | Starting materials | MW found (MH+) |
|---|---|---|---|---|
| 19 | 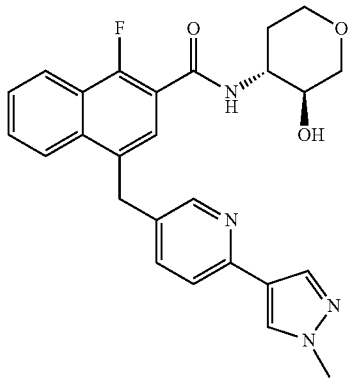 [SMILES: Cn1cc(-c2ccc(Cc3cc(C(=O)N[C@@H]4CCOC[C@H]4O)c(F)c4ccccc34)cn2)cn1] | 1-fluoro-N-[(3S,4R)-3-hydroxytetrahydropyran-4-yl]-4-[[6-(1-methylpyrazol-4-yl)-3-pyridyl]methyl]-naphthalene-2-carboxamide | 4-((6-chloropyridin-3-yl)methyl)-1-fluoro-N-((3S,4R)-3-hydroxytetrahydro-2H-pyran-4-yl)-2-naphthamide (example 25) | 461.5 |
| 20 | 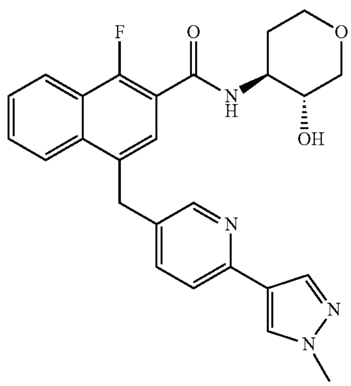 [SMILES: Cn1cc(-c2ccc(Cc3cc(C(=O)N[C@H]4CCOC[C@@H]4O)c(F)c4ccccc34)cn2)cn1] | 1-fluoro-N-[(3R,4S)-3-hydroxytetrahydropyran-4-yl]-4-[[6-(1-methylpyrazol-4-yl)-3-pyridyl]methyl]-naphthalene-2-carboxamide | 4-((6-chloropyridin-3-yl)methyl)-1-fluoro-N-((3R,4S)-3-hydroxytetrahydro-2H-pyran-4-yl)-2-naphthamide (example 25) | 461.5 |
| 21 | 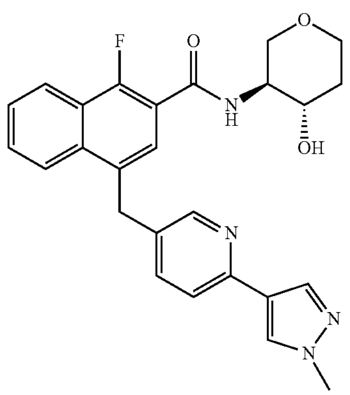 [SMILES: Cn1cc(-c2ccc(Cc3cc(C(=O)N[C@H]4COCC[C@@H]4O)c(F)c4ccccc34)cn2)cn1] | 1-fluoro-N-((3S,4S)-4-hydroxytetrahydro-2H-pyran-3-yl)-4-((6-(1-methyl-1H-pyrazol-4-yl)pyridin-3-yl)methyl)-2-naphthamide | 4-((6-chloropyridin-3-yl)methyl)-1-fluoro-N-((3S,4S)-4-hydroxytetrahydro-2H-pyran-3-yl)-2-naphthamide (example 4) | 461.4 |
| 22 | 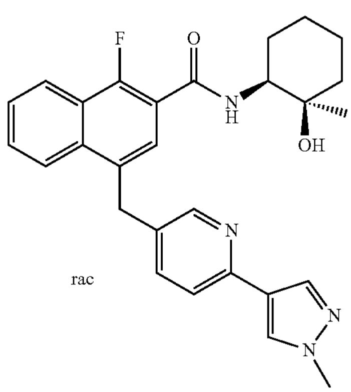 [SMILES: Cn1cc(-c2ccc(Cc3cc(C(=O)N[C@H]4CCCC[C@@]4(C)O)c(F)c4ccccc34)cn2)cn1] | 1-fluoro-N-((1SR,2RS)-2-hydroxy-2-methylcyclohexyl)-4-((6-(1-methyl-1H-pyrazol-4-yl)pyridin-3-yl)methyl)-2-naphthamide | 4-((6-chloropyridin-3-yl)methyl)-1-fluoro-N-((1SR,2RS)-2-hydroxy-2-methylcyclohexyl)-2-naphthamide (example 8) | 473.4 |

Example 23

1-Fluoro-N-((1SR,2SR)-2-hydroxycyclohexyl)-4-((6-methylpyridin-3-yl)methyl)-2-naphthamide

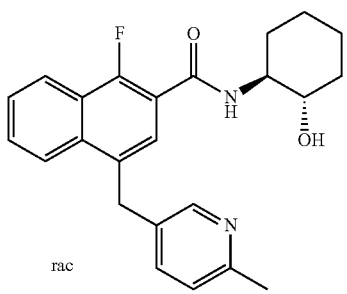 [SMILES: Cc1ccc(Cc2cc(C(=O)N[C@H]3CCCC[C@@H]3O)c(F)c3ccccc23)cn1]

To a solution of 4-((6-chloropyridin-3-yl)methyl)-1-fluoro-N-((1SR,2SR)-2-hydroxycyclohexyl)-2-naphthamide (example 1; 45.2 mg, 109 μmol) in THF (0.5 ml) was added 1,1-bis(diphenylphosphino)ferrocenedichloropalladium (II) (8.01 mg, 10.9 μmol). Dimethylzinc 1M in heptane (400 μl, 400 μmol) was added dropwise to the red suspension at 0° C. (exothermic reaction). The mixture was stirred at room temperature for 1 h 15 and then at 60° C. for 2 h. More catalyst 1,1-bis(diphenylphosphino)ferrocenedichloropalladium (II) (8.01 mg, 10.9 μmol) was added and the reaction was stirred at 60° C. for 4 h and then at room temperature for 2 days. During that time more dimethylzinc 1M in heptane (two times 400 μl, 400 μmol) was added. The mixture was quenched with saturated NaHCO$_3$ solution and diluted with EtOAc. The precipitate was filtered and the filtrate was extracted 3 times with EtOAc. The combined organic layers were dried over Na$_2$SO$_4$, filtered and concentrated. The crude product was purified by silica gel chromatography using a heptane/EtOAc gradient as eluent to obtain the title compound (16 mg, 38%) as light brown solid.

MS (m/e): 393.5 (M+H)$^+$

Example 24

4-((6-Cyclopropylpyridin-3-yl)methyl)-1-fluoro-N-((1S,2S)-2-hydroxycyclohexyl)-2-naphthamide

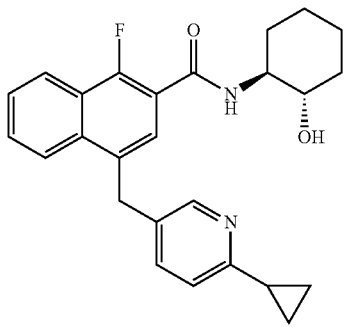 [SMILES: O=C(N[C@H]1CCCC[C@@H]1O)c1cc(Cc2ccc(C3CC3)nc2)c2ccccc2c1F]

To a mixture of 4-((6-chloropyridin-3-yl)methyl)-1-fluoro-N-((1S,2S)-2-hydroxycyclohexyl)-2-naphthamide (example 3; 40 mg, 96.9 μmol), cyclopropylboronic acid (16.6 mg, 194 μmol), tribasic potassium phosphate (72.0 mg, 339 mol), tricyclohexylphosphine (8.15 mg, 29.1 μmol) in degassed toluene (1 ml) and water (40 μl) was added palladium (II) acetate (3.26 mg, 14.5 μmol). The mixture was stirred at 125° C. for 2 hours in a sealed tube and then cyclopropylboronic acid (8.32 mg, 96.9 μmol) was added and the mixture was stirred at 125° C. for 2 hours. The mixture was diluted with ethyl acetate and washed with water, saturated solution of K$_2$CO$_3$ and saturated solution of NaCl. The aqueous layer was washed once with ethyl acetate. The combined extracts were dried over Na$_2$SO$_4$, filtered and concentrated. The crude product was purified by silica gel chromatography using a heptane/EtOAc gradient as eluent to obtain the title compound (5 mg, 12%) as light brown solid. MS (m/e): 419.5 (M+H)$^+$.

Example 25

4-[(6-chloropyridin-3-yl)methyl]-1-fluoro-N-[(3S,4R)-3-hydroxyoxan-4-yl]naphthalene-2-carboxamide

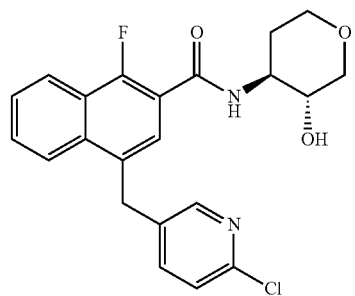 [SMILES: O=C(N[C@H]1CCOC[C@@H]1O)c1cc(Cc2ccc(Cl)nc2)c2ccccc2c1F]

The racemic 4-((6-chloropyridin-3-yl)methyl)-1-fluoro-N-((3RS,4SR)-3-hydroxytetrahydro-2H-pyran-4-yl)-2-naphthamide (example 4; 175 mg, 422 μmol) was separated on a Chiralpak AD column (D-7531) to provide the (−)-enantiomer (74 mg, 42%) as a white solid with MS (m/e): 415.4 (M+H)$^+$ and the desired (+)-enantiomer (77 mg, 44%) as a light yellow solid with MS (m/e): 415.5 (M+H)$^+$.

Example 26

4-((4-Cyano-4-(pyridin-2-yl)piperidin-1-yl)methyl)-1-fluoro-N-((1S,2S)-2-hydroxycyclohexyl)-2-naphthamide

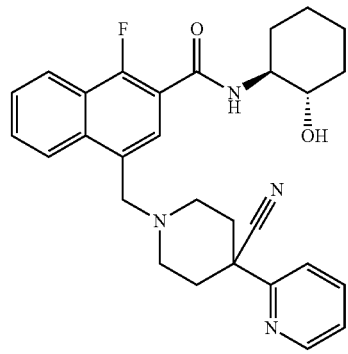 [SMILES: N#CC1(c2ccccn2)CCN(Cc2cc(C(=O)N[C@H]3CCCC[C@@H]3O)c(F)c3ccccc23)CC1]

Step 1: 4-Bromo-1-fluoro-N-((1S,2S)-2-hydroxycyclohexyl)-2-naphthamide

To a suspension of 4-bromo-1-fluoro-2-naphthoic acid (example A.1, step 1; 500 mg, 1.86 mmol) in dichloromethane (10 ml) were added (1S,2S)-2-aminocyclohexanol hydrochloride (282 mg, 1.86 mmol), BOP (1.09 g, 2.47 mmol) and triethylamine (564 mg, 776 µl, 5.57 mmol). The solution was stirred at room temperature for 21 hours. The solvent was removed in vacuo. The crude product was purified by silica gel chromatography using a heptane/EtOAc gradient as eluent to provide the title compound (328 mg, 48%) as white solid. MS (m/e): 366.4 (M)+, 368.4 (M+2)+

Step 2: 1-Fluoro-N-((1S,2S)-2-hydroxycyclohexyl)-4-vinyl-2-naphthamide

To a solution of tribasic potassium phosphate (291 mg, 1.37 mmol) in water (0.90 ml) was added 4-bromo-1-fluoro-N-((1S,2S)-2-hydroxycyclohexyl)-2-naphthamide (228 mg, 623 dioxane (2.25 ml), potassium trifluoro(vinyl)borate (128 mg, 953 mol), Pd$_2$(dba)$_3$ (28.5 mg, 31.1 mol) and tricyclohexylphosphine (17.5 mg, 62.3 mol). The mixture was stirred at 140° C. for 30 minutes under microwave irradiation twice. More potassium trifluoro(vinyl)borate (41.7 mg, 311 mol) was added and the mixture was stirred at 160° C. for 30 minutes under microwave irradiation, then diluted with water and ethyl acetate. The aqueous layer was extracted twice with ethyl acetate. The combined organic layers were dried over Na$_2$SO$_4$, filtered and concentrated. The crude product was purified by chromatography on Isolute® Flash-NH$_2$ silica gel (from Separtis) using a heptane/EtOAc gradient to obtain the title compound (96 mg, 49%) as off white solid.
MS (m/e): 314.4 (M+H)+.

Step 3: 1-Fluoro-4-formyl-N-((1S,2S)-2-hydroxycyclohexyl)-2-naphthamide

To a solution of 1-fluoro-N-((1S,2S)-2-hydroxycyclohexyl)-4-vinyl-2-naphthamide (20 mg, 63.8 mol) and ruthenium(III) chloride 0.035M in H$_2$O (63.8 µl, 2.23 mol) in MeCN (500 µl) and water (83.3 µl) was added sodium metaperiodate (27.3 mg, 128 mol) in portions.

The mixture was stirred at room temperature for 1 hour 40 minutes. The mixture was quenched with a saturated solution of Na$_2$S$_2$O$_3$ and the two layers were separated. The aqueous layer was extracted three times with EtOAc. The combined organic extract was washed with water and brine, dried over Na$_2$SO$_4$, filtered and concentrated. The crude product was purified by silica gel chromatography using a heptane/EtOAc gradient as eluent to obtain the title compound (11 mg, 56%) as white solid.
MS (m/e): 316.4 (M+H)+.

Step 4: 4-((4-Cyano-4-(pyridin-2-yl)piperidin-1-yl)methyl)-1-fluoro-N-((1S,2S)-2-hydroxycyclohexyl)-2-naphthamide To a solution of 1-fluoro-4-formyl-N-((1S,2S)-2-hydroxycyclohexyl)-2-naphthamide (40.5 mg, 128 µmol) and 4-(pyridin-2-yl)piperidine-4-carbonitrile (CAS 767263-33-2; 24.0 mg, 128 µmol) in 1,2-dichloroethane (1 ml) were added sodium triacetoxyhydroborate (38.1 mg, 180 µmol) and acetic acid (7.71 mg, 7.35 µl, 128 µmol). The mixture was stirred at room temperature under nitrogen atmosphere for 19 hours, then was quenched with a 1N NaOH solution and dichloro-methane was added. The two layers were separated and the aqueous layer was extracted twice with dichloromethane. The combined organic layers were dried over Na$_2$SO$_4$, filtered and concentrated. The crude product was purified by silica gel chromatography using a heptan/EtOAc gradient as eluent to provide the title compound (32 mg, 52%) as white solid. MS (m/e): 487.4 (M+H)+.

The invention claimed is:
1. A compound of formula I

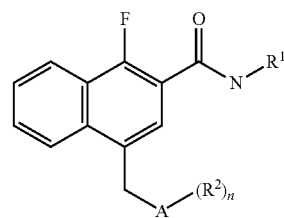

wherein
$R^1$ is $C_{4-6}$-cycloalkyl or $C_{4-6}$-heterocycloalkyl, which are optionally substituted by one or two substituents, selected from hydroxy or lower alkyl;
A is phenyl, pyridinyl or piperidinyl;
$R^2$ is hydrogen, halogen, lower alkyl, cyano, $C_{4-6}$-cycloalkyl, lower alkoxy, lower alkoxy substituted by halogen, or is a five- or six-membered heteroaryl, optionally substituted by lower alkyl; n is 1 or 2;
or a pharmaceutically acceptable acid addition salt, a racemic mixture or its corresponding enantiomer and/or optical isomers thereof.

2. A compound of formula I according to claim 1, wherein A is phenyl and the other substituents are as described in claim 1.

3. A compound of formula I according to claim 2, which compounds are
1-fluoro-N-((3RS,4SR)-3-hydroxytetrahydro-2H-pyran-4-yl)-4-(4-methylbenzyl)-2-naphthamide
4-benzyl-1-fluoro-N-((3RS,4SR)-3-hydroxytetrahydro-2H-pyran-4-yl)-2-naphthamide
4-(4-chlorobenzyl)-1-fluoro-N-((3RS,4SR)-3-hydroxytetrahydro-2H-pyran-4-yl)-2-naphthamide
4-(4-cyanobenzyl)-1-fluoro-N-((3RS,4SR)-3-hydroxytetrahydro-2H-pyran-4-yl)-2-naphthamide
1-fluoro-4-(2-fluoro-4-(1-methyl-1H-pyrazol-4-yl)benzyl)-N-((3RS,4SR)-3-hydroxytetrahydro-2H-pyran-4-yl)-2-naphthamide
1-fluoro-N-((3RS,4SR)-3-hydroxytetrahydro-2H-pyran-4-yl)-4-(4-(trifluoromethoxy)benzyl)-2-naphthamide
or
1-fluoro-N-((3RS,4SR)-3-hydroxytetrahydro-2H-pyran-4-yl)-4-(4-(1-methyl-1H-pyrazol-4-yl)benzyl)-2-naphthamide.

4. A compound of formula I according to claim 1, wherein A is pyridinyl and the other substituents are as described in claim 1.

5. A compound of formula I according to claim 4, wherein the compounds are
4-((6-chloropyridin-3-yl)methyl)-1-fluoro-N-((1SR,2SR)-2-hydroxycyclohexyl)-2-naphthamide
4-((6-chloropyridin-3-yl)methyl)-1-fluoro-N-((3RS,4SR)-3-hydroxytetrahydro-2H-pyran-4-yl)-2-naphthamide 4-((6-chloropyridin-3-yl)methyl)-1-fluoro-N-((1S,2S)-2-hydroxycyclohexyl)-2-naphthamide
4-((6-chloropyridin-3-yl)methyl)-1-fluoro-N-((3S,4S)-4-hydroxytetrahydro-2H-pyran-3-yl)-2-naphthamide
4-((6-chloropyridin-3-yl)methyl)-1-fluoro-N-((1S,2S)-2-hydroxycyclopentyl)-2-naphthamide
4-((6-chloropyridin-3-yl)methyl)-1-fluoro-N-((1S,2R)-2-hydroxycyclopentyl)-2-naphthamide
4-((6-chloropyridin-3-yl)methyl)-1-fluoro-N-((1SR,2SR)-2-hydroxy-2-methylcyclohexyl)-2-naphthamide
4-((6-chloropyridin-3-yl)methyl)-1-fluoro-N-((1SR,2RS)-2-hydroxy-2-methylcyclohexyl)-2-naphthamide
4-((6-chloropyridin-3-yl)methyl)-1-fluoro-N-((1SR,2RS)-2-hydroxycyclohexyl)-2-naphthamide
1-fluoro-N-((1S,2 S)-2-hydroxycyclhexyl)-4-((6-(1-methyl-1H-pyrazol-4-yl) pyridin-3-yl)methyl)-2-naphthamide
1-fluoro-N-((3RS,4SR)-3-hydroxytetrahydro-2H-pyran-4-yl)-4-((6-(1-methyl-1H-pyrazol-4-yl)pyridin-3-yl)methyl)-2-naphthamide
1-fluoro-N-[(3S,4R)-3-hydroxytetrahydropyran-4-yl]-4-[[6-(1-methylpyrazol-4-yl)-3-pyridyl]methyl]naphthalene-2-carboxamide
1-fluoro-N-[(3R,4S)-3-hydroxytetrahydropyran-4-yl]-4-[[6-(1-methylpyrazol-4-yl)-3-pyridyl]methyl]naphthalene-2-carboxamide
1-fluoro-N-((3S,4 S)-4-hydroxytetrahydro-2H-pyran-3-yl)-4-((6-(1-methyl-1H-pyrazol-4-yl)pyridin-3-yl)methyl)-2-naphthamide
1-fluoro-N-((1SR,2RS)-2-hydroxy-2-methylcyclohexyl)-4-((6-(1-methyl-1H-pyrazol-4-yl)pyridin-3-yl)methyl)-2-naphthamide
1-fluoro-N-((1SR,2SR)-2-hydroxycyclohexyl)-4-((6-methylpyridin-3-yl)methyl)-2-naphthamide
4-((6-cyclopropylpyridin-3-yl)methyl)-1-fluoro-N-((1S,2S)-2-hydroxycyclohexyl)-2-naphthamide
or 4-[(6-chloropyridin-3-yl)methyl]-1-fluoro-N-[(3S,4R)-3-hydroxyoxan-4-yl]naphthalene-2-carboxamide.

6. A compound of formula I according to claim 1, wherein A is piperidinyl and the other substituents are as described above.

7. A compound of formula I according to claim 6, wherein the compound is 4-((4-cyano-4-(pyridin-2-yl)piperidin-1-yl)methyl)-1-fluoro-N-((1S,2 S)-2-hydroxycyclohexyl)-2-naphthamide.

8. A process for the manufacture of a compound of formula I as defined in claim 1, which process comprises reacting a compound of formula 1:

(1)

with a compound of formula 2:

$$R^1NH_2 \quad (2)$$

in the presence of an activating agent, selected from BOP (Benzotriazol-1-yloxy)tris(dimethylamino)phosphonium hexafluorophosphate or thionyl chloride, to a compound of formula I:

(I)

wherein the substituents are as defined in claim 1,
and, if desired, converting the compounds obtained into pharmaceutically acceptable acid addition salts.

9. A compound manufactured by the process of claim 8.

10. A pharmaceutical composition comprising a compound according to claim 1 and a pharmaceutical acceptable carrier and/or adjuvant.

11. Pharmaceutical composition comprising a compound according to claim 1 and a pharmaceutical acceptable carrier and/or adjuvant for use in the treatment of Alzheimer's disease, cognitive impairment, schizophrenia, pain or sleep disorders.

12. A method for the treatment of Alzheimer's disease, cognitive impairment, schizophrenia, pain or sleep disorders, which method comprises administering an effective amount of a compound as defined in claim 1.

* * * * *